United States Patent
Nicoletti et al.

(10) Patent No.: US 8,207,206 B2
(45) Date of Patent: Jun. 26, 2012

(54) (S,R)-3-PHENYL-4,5 DIHYDRO-5-ISOXAZOLE ACETIC ACID-NITRIC OXIDE AND USE THEREOF AS ANTI-CANCER AND ANTIVIRAL AGENT

(75) Inventors: Ferdinando Nicoletti, Cannizzaro (IT); Yousef Al-Abed, Locust Valley, NY (US); Gianni Garotta, Lucinges (FR)

(73) Assignee: OncoNOx APS, Copenhagen (DK)

( * ) Notice: Subject to any disclaimer, the term of this patent is extended or adjusted under 35 U.S.C. 154(b) by 0 days.

(21) Appl. No.: 12/599,221

(22) PCT Filed: May 6, 2008

(86) PCT No.: PCT/EP2008/003626
§ 371 (c)(1),
(2), (4) Date: May 19, 2010

(87) PCT Pub. No.: WO2008/138516
PCT Pub. Date: Nov. 20, 2008

(65) Prior Publication Data
US 2010/0305176 A1  Dec. 2, 2010

Related U.S. Application Data

(60) Provisional application No. 60/924,321, filed on May 9, 2007.

(51) Int. Cl.
*A61K 31/4245* (2006.01)
*C07D 271/08* (2006.01)

(52) U.S. Cl. ........................................ 514/364; 548/125

(58) Field of Classification Search ........................ None
See application file for complete search history.

(56) References Cited

FOREIGN PATENT DOCUMENTS

WO   WO-9524398 A1    9/1995
WO   WO-2006097273 A1 9/2006

OTHER PUBLICATIONS

Pinedo et al. The Oncologist, 2000, 5 (suppl. 1): pp. 1-2.*
McMahon, The Oncologist, 2000, 5 (suppl. 1): pp. 3-10.*
Huff et al. J. Med. Chem. 34(8) 1991. p. 2305-2314.*
The Merck Manual, 16th Ed., 1999, pp. 52-55.*
Dorwald, F.A. Side Reactions in Organic Synthesis, 2005, Wiley:VCH, Weinheim, p. IX of preface.*

* cited by examiner

*Primary Examiner* — Rebecca Anderson
*Assistant Examiner* — Alicia L Otton
(74) *Attorney, Agent, or Firm* — Arent Fox LLP

(57) ABSTRACT

The present invention relates to an isoxazole derivative, the compound of formula (I)

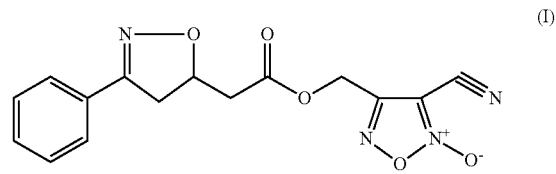

herein after referred to as GIT27-NO, which is the NO-donating structurally modified form of (S,R)-3-phenyl-4,5-dihydro-5-isoxazole acetic acid, herein after referred to as VGX-1027. Treatment of three tumor cell lines, rat astrocytoma C6, mouse fibrosarcoma L929, and mouse melanoma B16 cells with GIT27-NO resulted in a significant reduction of cell respiration and of number of viable cells, while VGX-1027 was completely ineffective. Hemoglobin, which act as NO-scavenger, restored cell viability, thus indicating the NO-mediated tumoricidal effect of compound (I). GIT27-NO triggered apoptotic cell death in L929 cell cultures, while autophagic cell death is mainly responsible for the diminished viability of C6 and B16 cells. Moreover, GIT27-NO induced the production of reactive oxygen species which can be neutralized by antioxidant N-acetyl cysteine (NAC), indicating that reactive oxygen species (ROS) are at least partly involved in the reduction of cell viability. The anti-tumor activity of GIT27-NO is mediated through activation of MAP kinases (ERK1/2, p38 and JNK) in cell-specific manner. The role of MAP kinases was further confirmed by specific inhibitors of these molecules, PD98059, SB202190, and SP600125. Finally, in vivo treatment with GIT27-NO significantly reduced tumor growth in syngeneic C57BL/6 mice implanted with B16 melanoma.

8 Claims, 6 Drawing Sheets

(S,R)-3-PHENYL-4,5 DIHYDRO-5-ISOXAZOLE ACETIC ACID-NITRIC OXIDE AND USE THEREOF AS ANTI-CANCER AND ANTIVIRAL AGENT

CROSS-REFERENCE TO RELATED APPLICATION

This application is a National Stage entry of International Application No. PCT/EP2008/003626, filed May 6, 2008, the disclosure of the prior application is hereby incorporated in its entirety by reference.

BACKGROUND OF THE INVENTION

Nitric oxide (NO) is a highly reactive molecule implicated in numerous physiological and pathological processes. The role of NO in vasodilatation, neurotransmission and immunity is complex in many aspects (Tarr 2006). This molecule is also known as the main actor of nonspecific anti-tumor immune responses (Roshni 2003). However, recent studies show that interplay with cancer cells is more complex than it was believed to be before. NO is able to inhibit, but also to promote, tumor expansion and metastases (Tarr 2006, Lechner 2005). The outcome of tumor —NO interactions depends on the NO source, the type of exposed cell, the localization of NO within the cell, the duration of NO exposure, and the presence of other free radical species with which NO may interact (Tarr 2006). In general, NO produced by host macrophages and NK cells mediates the anti-tumor response (Roshni 2003). In contrast, the pro-tumorigenic role of NO is ascribed to the intrinsic potential of tumor cells to generate this molecule and accordingly auto-regulate their own growth (Lechner 2005). NO directly influences the growth of tumor cells through electron donation and reaction with transition metals such as iron, zinc and copper and therefore modifies the enzymatic and transcriptional factor activity. Through generation of new radicals, NO indirectly mediates further destruction of cellular components (Li 2005, Tarr 2006, Lechner 2005).

Several active antitumour agents are nowadays available; however, cancer drug design is still a great challenge for numerous scientists. The search is aimed at finding substances with improved efficacy, reduced side-effects and suitable administration routes. A novel therapeutic approach of particular interest in the prevention and/or treatment of cancer is represented by NO-donating nonsteroidal antiinflammatory drugs (NO-NSAIDs).

NO-NSAIDs consist of NSAIDs to which a NO-donating group is covalently attached via an aromatic or aliphatic spacer (see Rigas and Kashfi 2004). Although these drugs share some pharmacological properties with their parent compounds, current data suggest that their structural modification is responsible for enhanced potency and diminished toxicity (Keeble 2002).

NO-NSAIDs are effective in the Alzheimer's disease and in cardiovascular, rheumatological, and lung diseases (Del Soldato et al 1999). The combination of cyclooxygenase-inhibition property of NSAIDs with tumoricidal potential of NO makes these drugs a perfect candidate for the treatment of malignant diseases (see Rigas and Kashfi 2004).

It has been demonstrated that different NO-NSAIDs affect cancer cell growth both in vitro and in vivo. These drugs possess strong anti-proliferative and pro-apoptotic potential against human bladder, colon, prostate, lung, pancreatic, and tongue cancer cells and leukemia cell lines (Kashfi et al 2003, Yeh 2004, Huguenin 2005, Huguenin 2004a, Huguenin 2004b, Gao 2005, Nath 2004, Spiegel 2005). Moreover, NO-aspirin and NO-indomethacin are effective against gastrointestinal cancerogenesis in rats and mice (Bak 1998, Williams 2004, Rao). NO-donating aspirin prevented pancreatic cancer in a hamster tumor model (Ouyang 2006). The exact mechanisms responsible for the action of these drugs are not yet completely understood, but it is believed that the potential targets are NF-κB, inducible NO-synthase and cyclooxygenase (Rigas rew 2004).

It has recently been shown that an isoxazoline compound, (S,R)-3-phenyl-4,5-dihydro-5-isoxasole acetic acid (VGX-1027) possesses strong immunomodulatory properties. VGX-1027 protects mice against the lethal effects of LPS through inhibition of TNF-α synthesis from macrophages and/or T-cells (Stojanovic et at in press). Moreover, administration of VGX-1027 to NOD mice with spontaneous or accelerated forms of diabetes or with immunoinflammatory diabetes induced with multiple low doses of streptozotocin, significantly reduces diabetes progress (Stosic-Grujicic et al 2006).

DESCRIPTION OF THE INVENTION

Figure 1:
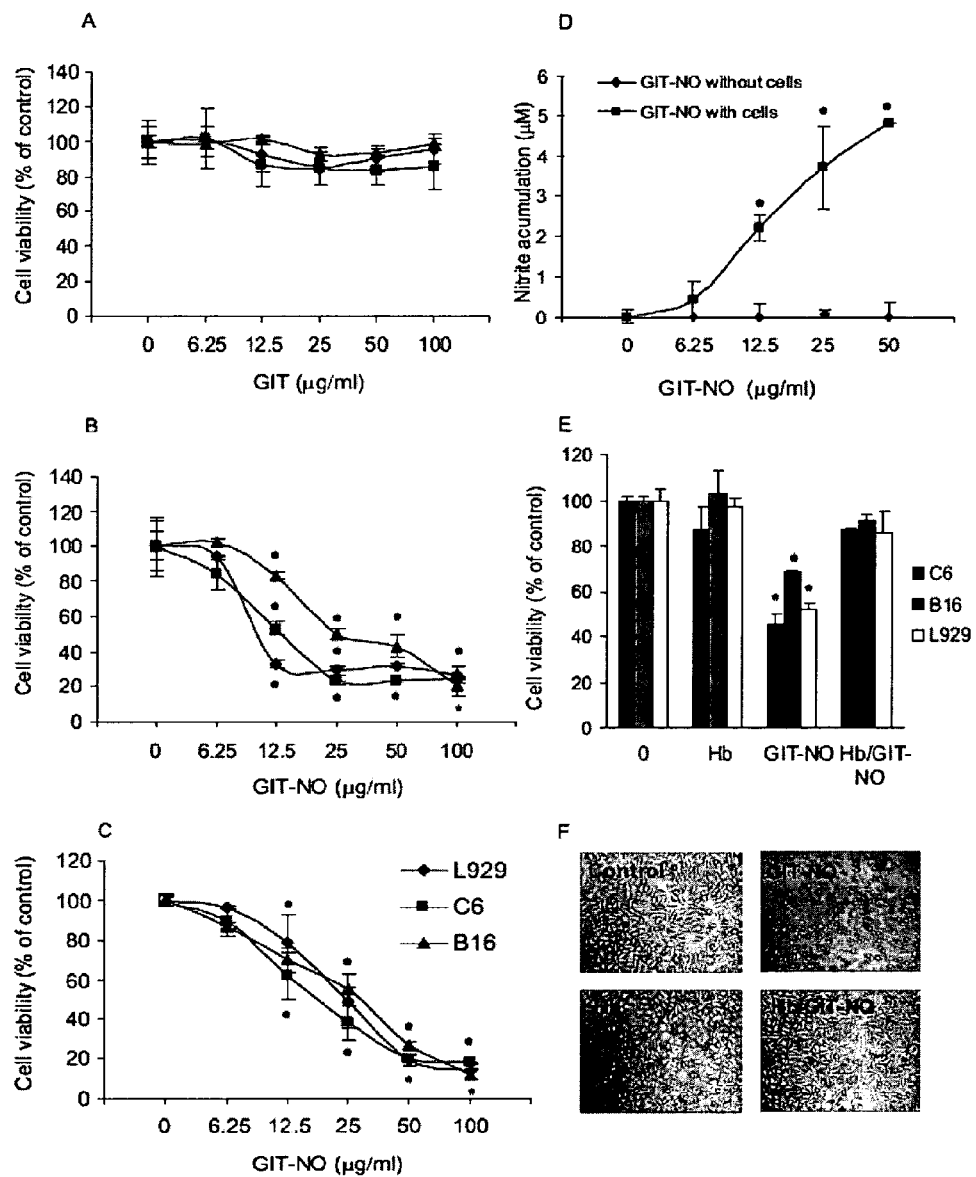
FIG. 1. GIT27-NO down-regulates tumor cell viability through NO release. B16 melanoma, L929 fibrosarcoma and C6 astrocytoma cells ($1\times10^4$/well) were treated with different concentration of either VGX-1027 or GIT27-NO. After 24 h cultivation cell viability was determined by MIT (A, B) and CV test (C). Accumulation of nitrites in culture media (D) was detected after 24 h treatment of C6 cells in the presence of GIT27-NO, or in indicated dilutions of GIT27-NO without cells. MTT assay (E) and light microscopy analyses (F) of C6 cells treated for 24 h with hemoglobin (12.5 μM) in parallel with GIT27-NO (25 mg/ml) were performed after the 24 h incubation. The data are presented as mean±SD from representatives of three independent experiment. *$p<0.05$, refers to untreated cultures.

The present invention relates to an isoxazoline compound of formula (I)

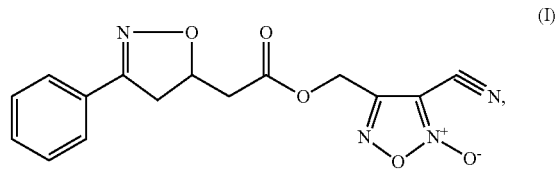

herein after also referred to as (GIT27-NO), which can be synthesized according to the following scheme.

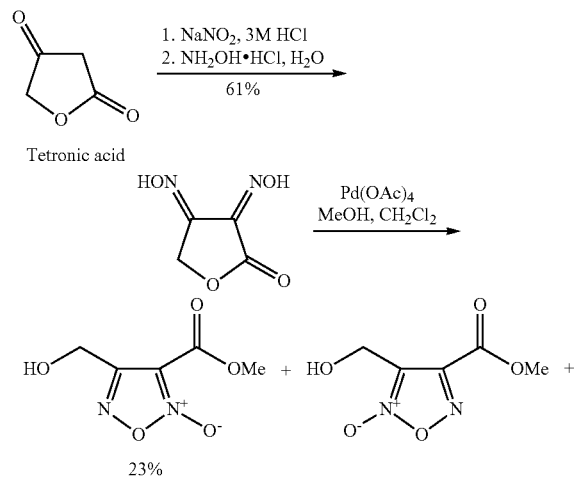

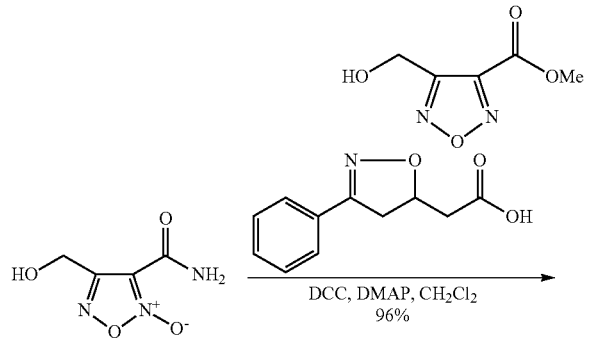

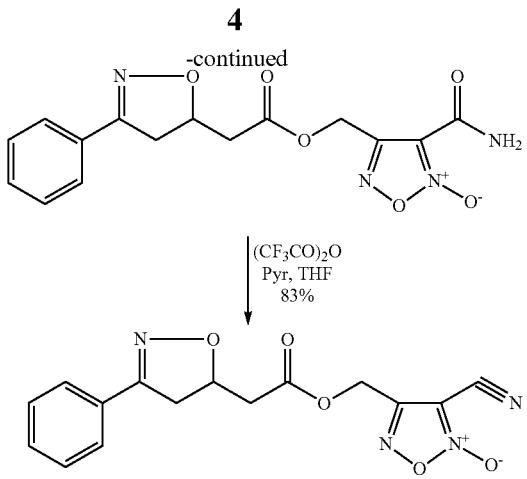

Compound (I) proved effective as antitumor and as antiviral agent and in prevention and treatment of gastric ulcer in animal models. It can therefore be used for the preparation of antitumor and antiviral pharmaceutical compositions as well as for compositions designed to treat gastrointestinal ulcers, hemorrhagic shock and organ damage associated with ischemia-reperfusion which can be prepared with excipients and/or vehicles and according to procedures known to those skilled in the art. Pharmaceutical compositions parenteral, oral and topical compositions, as well as eye drops for the treatment of viral infections of the eye.

Object of the present invention is also a method for the treatment of tumor pathologies and viral infections comprising the administration of an effective amount of compound (II); the dose and the time of administration be determined by the physician according to the patient's needs.

The invention also relates to the precursor of compound (I), the compound of formula (II)

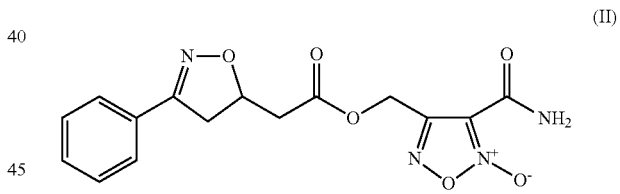

which is also able to release NO and proved effective as antitumor and antiviral agent.

The invention will be now illustrated in greater detail in the following experimental section.

EXPERIMENTAL SECTION

Chemistry

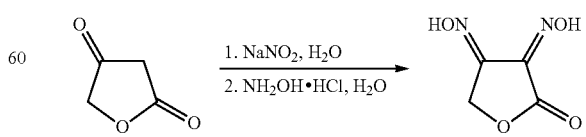

This reaction was carried out according to the procedure disclosed in: Tetronic acids and derivatives; Part VI. A convenient synthesis of new 4-oxo-2-phenyl-2H-4,6-dihydrofuro[3,4-d]triazole and 4-oxo-4,6-dihydrofuro[3,4-c]furazan systems. Parick Pollet, Suzanne Gelin. *Synthesis* 1979, 977-979.

Sodium nitrite (6.9 g, 100 mmoles) was added in portions to a stirred solution of tetronic acid (10 g, 100 mmoles) in 3M HCl (60 mL). The purple solution was stirred for 15 min at room temperature and then added dropwise to a virgorously stirred solution of hydroxylamine hydrochloride (13.9 g, 200 mmoles) in water (150 mL). The purple coloration gradually faded away at room temperature and 3,4-bis[hydroxylimino]-2-oxotetrahydrofuran (9.11 g, 63%) precipitated as white needles.

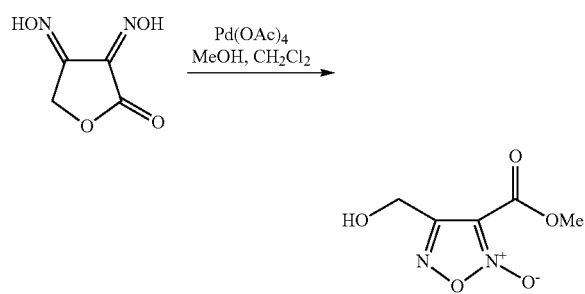

This reaction was carried out according to the procedure disclosed in DE4401150A1.

Into a mixture of 3,4-bis[hydroxylimino]-2-oxotetrahydrofuran (5.5 g, 38.2 mmoles), $CH_2Cl_2$ (60 mL) and methanol (21 mL) Pb(OAc)$_4$ (16.9 g, 38.2 mmoles) was added at 5-10° C. After stirring at room temperature for 2 h, triethylamine (5 mL, 38.2 mmoles) was added and stirred for further 30 min. $CH_2Cl_2$ (150 mL) was added and the mixture was washed with water. The $CH_2Cl_2$ extract was dried with $Na_2SO_4$ and concentrated in vacuo. The residue was stirred with isopropyl acetate and filtered and the filtrate was recrystallized from isopropyl acetate to afford 4-hydroxymethyl-2-oxyfurazan-3-carboxymethylester (1 g, 15%). $^1$H NMR (300 MHz, $C_3D_6O$) δ 3.94 (3H, s), 4.85 (2H, s). $^{13}$C NMR (75 MHz, $C_3D_6O$) δ 52.6, 56.2, 107.9, 156.9, 157.8.

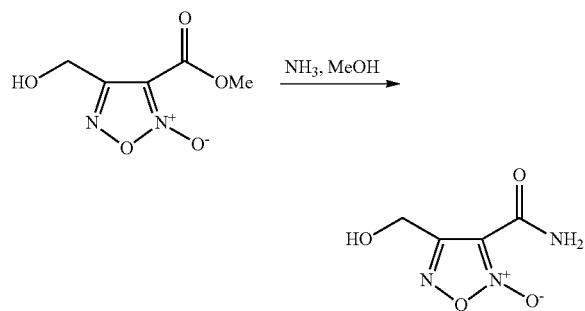

4-Hydroxymethyl-2-oxyfurazan-3-carboxymethylester (611 mg, 3.51 mmole) was added with 2 M ammonia in MeOH (25 mL). The solution was stirred for 2 h at room temperature. The reaction mixture was concentrated in vacuo to afford 4-hydroxy-2-oxyfurazan-3-carboxylic acid amide (551 mg, 98%). $^1$H NMR (300 MHz, $C_3D_6O$) δ 4.80 (2H, s). $^{13}$C NMR (75 MHz, $C_3D_6O$) δ 56.1, 111.3, 157.1, 158.8.

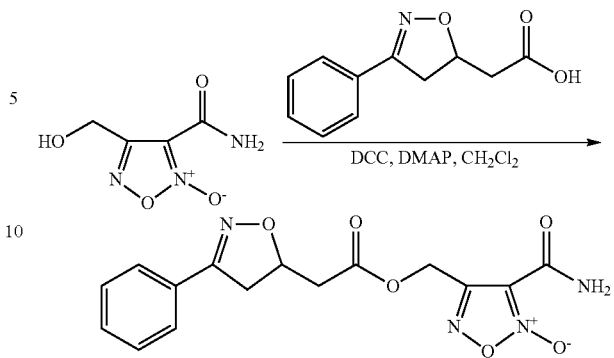

A stirred solution of 4-hydroxy-2-oxyfurazan-3-carboxylic acid amide (170 mg, 1.07 mmole), (3-phenyl-4,5-dihydro-isoxazol-5-yl) acetic acid (262 mg, 1.28 mmole) and DMAP (65 mg, 0.53 mmole) in $CH_2Cl_2$ (10 mL) was added with DCC (264 mg, 1.28 mmole). After stirring at room temperature for 24 h, diethyl ether (50 mL) was added and the mixture was filtered through Celite. Concentration of the filtrate followed by flash column chromatography (4:1 EtOAc:hexane) of the residue afforded the desired ester (356 mg, 96%). $^1$H NMR (300 MHz, $C_3D_6O$) δ 2.78 (d, J=5 Hz, 1H), 2.91 (d, J=5 Hz, 1H) 3.30 (d, J=8 Hz, 1H), 3.62 (d, J=8 Hz, 1H), 5.14 (m, 1H), 5.48 (s, 2H), 7.42 (m, 3H), 7.68 (d, J=8 Hz, 2H). $^{13}$C NMR (75 MHz, $C_3D_6O$) δ 39.2, 39.4, 57.1, 77.5, 110.7, 126.6, 128.7, 130.0, 154.9, 155.8, 156.5, 169.3.

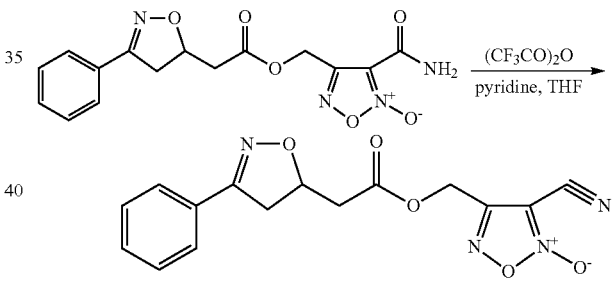

Trifluoroacetic anhydride (0.3 mL, 2.02 mmoles) was added dropwise to a stirred and ice-salt cooled solution of (3-phenyl-4,5-dihydro-isoxazol-5-yl) acetic acid-4-carbamoyl-5-oxyfurazan-3-ylmethyl ester (348 mg, 1.01 mmoles) and dry pyridine (0.15 mL, 2.02 mmoles) in THF (10 mL). The cooling bath was removed, and stirring was continued for 1 h at room temperature. The reaction mixture was poured in water, acidified with 10% HCl$_{(aq)}$ and extracted with EtOAc. The combined organic layers were dried with $Na_2SO_4$ and evaporated to afford a residue which was purified by flash chromatography to obtain the desired nitrile (275 mg, 83%). $^1$H NMR (300 MHz, CDCl$_3$) δ 2.79 (d, J=5 Hz, 1H), 2.93 (d, J=5 Hz, 1H), 3.12 (d, J=8 Hz, 1H), 3.55 (d, J=8 Hz, 1H), 5.11 (m, 1H), 5.29 (s, 2H), 7.38 (m, 3H), 7.59 (d, J=8 Hz, 2H). $^{13}$CNMR (75 MHz, CDCl$_3$) δ 39.2, 40.2, 56.2, 76.2, 96.5, 105.2, 126.8, 128.9, 130.6, 152.5, 156.8, 169.2.

Pharmacology

The anti-tumor effect of both parent and NO-conjugated compound (I) was studied in vitro on mouse fibrosarcoma L929, mouse melanoma B16 and rat astrocytoma C6 cell lines, as well as in an in vivo model of melanoma in C57BL/6 mice.

Materials and Methods

Reagents, Cells and Animals

Acridin orange was obtained from Labo-Moderna, France. Carboxyfluorescein diacetate succinimidyl ester (CFSE) was from Molecular Probes (Eugene, USA). Bis-tyrphostin was from ICN Biomedicals (Irvine, Calif.). All other chemicals used in the experiments were purchased from Sigma (St. Louis, USA). GIT27-NO was stored at +4° C. at a concentration of 5 µg/ml in 2.5% DMSO in $H_2O$ and was diluted in the culture medium immediately before use. Control cell cultures contained the same amount of DMSO as solution with the highest concentration of GIT27-NO used in the experiment.

Rat glioma cell line C6 was a kind gift from Dr. Pedro Tranque (Universidad de Castilla-La Mancha, Albacete, Spain), murine melanoma B16 cell line was a kind gift from Dr. Sinisa Radulovic (Institute for Oncology and Radiology of Serbia, Belgrade, Serbia) while mouse fibrosarcoma L929 was obtained from the European Collection of Animal Cell Cultures (Salisbury, UK). Cells were grown in HEPES-buffered RPM, 1640 medium supplemented with 5% FCS, 2 mM glutamine, 0.01% sodium pyruvate, $5 \times 10^{-5}$ M 2-mercaptoethanol and antibiotics (culture medium) at 37° C. in a humidified atmosphere with 5% CO. After conventional trypsinization the cells were seeded at a concentration of $10^4$ cells/well in a 96-well plate, of $2 \times 10^5$ cells/well in a 6-well plate or at $3 \times 10^4$ cells/well in a 4-well chamber slide, cultivated overnight, and then exposed to the test compound.

Inbred C57BL/6 mice were from our own facility at the Institute for Biological Research "Sinisa Stankovic" (Belgrade, Serbia) and kept under standard laboratory conditions (non specific pathogen free) with free access to food and water. The handling of animals and the study protocol were in accordance with international guidelines and approved by the local Institutional Animal Care and Use Committee.

MTT, CV, and CFSE Staining

The cells were seeded in flat-bottom 96-well plates ($10^4$ cells/well) in a final volume of 200 µl of culture medium, incubated overnight, then treated with different concentrations of the test compound. After 24 h incubation, cell viability was assessed using 3-4,5-dimethylthiazol-2-yl)-2,5-diphenyltetrazolium bromide (MTT) test, based on the mitochondrial-dependent reduction of MTT to formazan, or by crystal violet (CV) staining of adherent cells, as previously described (Mijatovic et al CMLS 2004). The results are presented as % of control values obtained in untreated cultures. The rate of cell proliferation was also determined using flow cytometric analysis of cells labeled with CFSE (Kang 2005). The cells were detached, added with 1.5 µM CFSE and allowed to stand for 15 min at 37° C., then washed twice and seeded in 6-well plates at $2 \times 10^5$. The cells were treated with the compound for 24 and 48 h, trypsinized and washed twice. Finally, the cells were resuspended in PBS and analyzed by flow cytometry. Green fluorescence emission from cells illuminated with excitation light of 488 nm was measured with a FACS Calibur (BD, Heidelberg, Germany) and analyzed using the CellQuest software.

Determination of Cell Death

As a marker of necrotic cell death, the release of intracellular enzyme LDH, which mediates the conversion 2,4-dinitrophenylhydrazine into visible hydrazone precipitate in the presence of pyruvate, was measured. The cells were seeded in flat-bottom 96-well plates as indicated above and the assay was performed after 24 h incubation, as previously described (Decker et al). The percentage of dead cells was determined using the following formula: $[(E-C)/(T-C)] \times 100$, wherein E is the experimental absorbance of treated cultures measured at 492 nm, C is the absorbance of supernatants of control untreated cells, and T is the absorbance corresponding to the maximal (100%) LDH release of Triton-lysed cells. Cell cycle analysis and apoptosis detection were carried out exactly as described in the literature (Mijatovic CMLS 2005). Acidic vesicular organelles, which characterise autophagy, are stained by vital dye acridin orange. The intensity of red fluorescence is proportional to the acidity and volume of the organelles, while the cytoplasm and nucleolus emits bright green and dim red (Kanzawa 2004). For the detection of autophagy the cells were cultivated in 6-well plates as previously described, detached and stained with 1 µg/ml acridin orange for 15 min at RT. At the end of the incubation period the cells were washed and finally resuspended in PBS. Green (510-530 nm) and red (>650 nm) fluorescence emission from $10^4$ cells illuminated with blue (488 nm) excitation light was measured with a FACS Calibur and analyzed using CellQuest software.

Measurement of ROS and Nitrite Accumulation

The cells grown in the 6-well plate were stained with 1 µM dihydrorhodamine 123 (DHR) 20 min before the treatment with the test compound. At the end of the cultivation period the cells were detached, washed and resuspended in PBS. Analysis of ROS release was performed with a FACSCalibur and analyzed using CellQuest Pro software (Kaludjerovic 2005).

Nitrite accumulation was measured by Griess reaction as previously described (Mijatovic et al CMLS 2004).

Cell-Based ELISA

Activation of MAP kinases (p38 MAPK, extracellular signal-regulated kinase—ERK, and Jun-N-terminal kinase—JNK) or nuclear factor-κB (NF-κB) was determined by means of a slightly modified method of cell-based ELISA by Versteeg et al. (Versteeg 2000). Since MAP kinases are activated by phosphorylation, and phosphorylation of the inhibitory subunit IκB is a necessary step for NF-κB activation, we used antibodies specific for phosphorylated forms of MAP kinases (p-p38, p-ERK and p-JNK) and IκB (p-IκB). The cells were grown overnight in 96-well flat-bottom plates in a culture medium containing 0.5% FCS and then treated with the test compound diluted in conventional culture medium. At the end of treatment period the cells were fixed in 4% parformaldehyde, endogenous peroxydase was quenched with 1% $H_2O_2$ in PBS containing 0.1% Triton X-100 (PBST), and unspecific binding of antibodies was blocked with a PBST solution containing 10% FCS. Primary mouse monoclonal antibodies specific for rat/mouse p-ERK, p-p38, p-JNK, p-IκB (1:200; all from Santa Cruz Biotechnology, Santa Cruz, Calif.) were applied in PBST supplemented with 2% bovine serum albumine (PBSTB), followed by secondary peroxidase-conjugated goat anti-mouse IgG (1:2500 in PBSTB; USB corporation, Cleveland, Ohio) for anti-p-ERK, anti-p-JNK and anti-p-IκB, or anti-mouse IgM (1:4000; USB corporation) for detection of anti-p-p38. Incubation with antibodies was carried out at 37° C. for 1 h. After 15 min incubation with peroxydase substrate TMB and subsequent addition of 0.1 M HCl, the absorbance at 450 nm was measured in an automated microplate reader. To enable comparison between treatment and control, the resulting absorbances were corrected for the cell number determined by crystal violet staining, as described in the original protocol. The results are presented as relative expression in comparison with the control value, which was arbitrarily set to 1.

Induction of Melanoma in C57BL/6 Mice and Treatment with GIT27-NO

Primary tumors were induced by subcutaneous (s.c) injection of $2 \times 10^5$ B16 melanoma cells in the dorsal right lumbosacral region of syngeneic C57BL/6 mice. Tumor growth was observed daily, and treatment with GIT27-NO was started from the day when the first tumor was palpable (day 10). GIT27-NO was prepared immediately before treatment and was applied i.p. at a dose of 0.5 mg/mouse for 14 consecutive days. The animals were observed until day 30, then sacrificed and tumor growth was determined by three-dimensional measurements of individual tumors from each mouse. Tumor volume was calculated using the following formula: $[0.52 \times a \times b^2]$, where a is the longest and b is the shortest diameter (Smagur et al).

Hepatitis Induced by Concanavalin (ConA) Injection in NMRI Mice and Treatment with Git27-NO ConA-induced hepatitis is a cell-mediated immunoinflammatory condition similar to different immunoinflammatory conditions of liver diseases in humans that can be induced in mice by a single intravenous injection of ConA. This disease is characterized by a marked increase in the plasma levels of transaminase shortly (8-24 hours) after ConA challenge and simultaneous infiltration of the liver with neutrophils, macrophages and T cells followed by apoptosis and necrosis of the hepatocytes.

Hepatitis was induced by ConA (Sigma Chemical, St. Louis, Mo.) injection into the tail veins in six to 9 weeks Naval Medical Research Institute (NMRI) male mice. Four groups of mice were treated or i.p. with Git27-NO at the doses of 0.5 and 1 or p.o. at 5 mg/mouse or with the vehicle, −24 and −1 hours prior to ConA. The animals were sacrificed for blood collection 8 hours after Con A injection and plasma alanine aminotransferase (ALT) activity was determined by a standard photometric assay using a bichromatic analyzer.

Statistical Analysis

The results are presented as means+/−SD of triplicate observations from one representative of at least three experiments with similar results, unless indicated otherwise. The significance of the differences between various treatments was assessed by variance analysis (ANOVA), followed by Student-Newman-Keuls test or Mann-Whitney U-test for evaluating GIT27-NO efficacy in vivo. A p value less than 0.05 was considered to be significant.

Results

Evaluation of Anti-Tumor Activity of GIT27-NO Versus VGX-1027

To evaluate the antitumor effect of VGX-1027 and GIT27-NO, we incubated three malignant cell lines, C6 rat astrocytoma, L929 mouse fibrosarcoma and B16 mouse melanoma, for 24 h with different concentrations of the drugs and then cell viability was determined by MTT and CV tests. As shown in FIG. 1A, parent compound VGX-1027 did not affect the viability of tumor cells. On the other hand, treatment of all three cell lines with GIT27-NO at the same concentration range (FIG. 1B) caused dose-dependent reduction of mitochondrial respiration. The effect was evaluated in terms of reduction of cell number as estimated by CV (FIG. 1C). Thus, it was evident that chemical modification of inactive VGX-1027 resulted in a new compound with strong tumoricidal activity. Considering this, we excluded VGX-1027 from further investigation. To evaluate the connection between the antitumor effect of compound (I) and its ability to release NO, we compared the accumulation of nitrites in cell culture supernatants with their quantity in culture media alone. As shown in FIG. 1D, GIT27-NO failed to release NO and to form nitrites in the absence of cells, while a significant amount of nitrites was observed after treatment of the cells. These data suggest that, unlike conventional exogenous NO-donors, GIT27-NO is not capable of spontaneous release of NO. To investigate the role of NO in GIT27-NO mediated down-regulation of cell viability, we cultivated tumor cells in parallel with the NO-scavenger hemoglobin. The viability of cells treated with GIT27-NO in such conditions was almost completely restored, indicating the importance of NO in drug-mediated cytotoxicity (FIG. 1E). This phenomenon was further visualized by light microscopy (FIG. 1F).

GIT27-NO Induces Distinct Types of Cell Death

Figure 2:
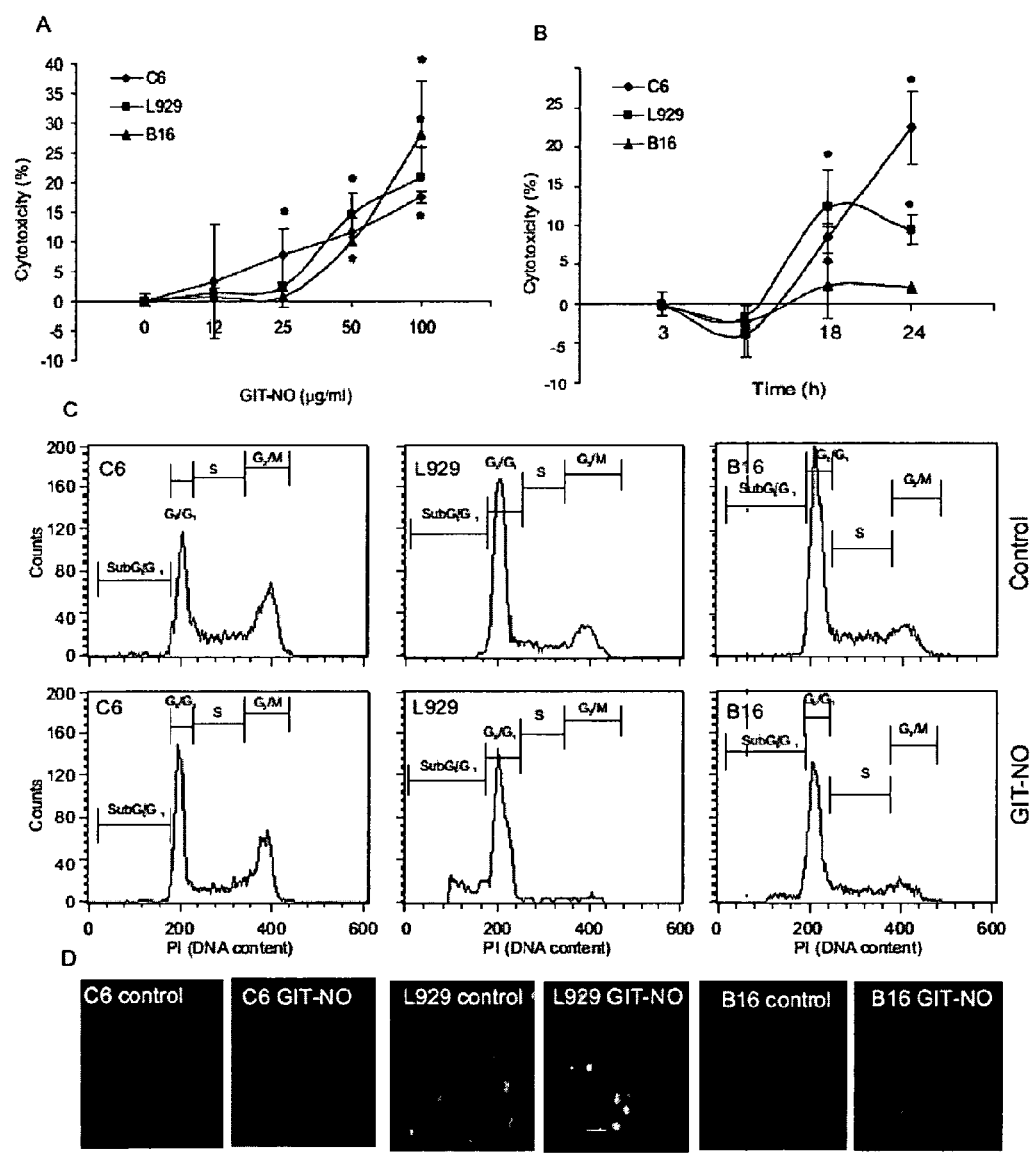
FIG. 2. Different cytotoxic efficiency towards C6, B16 and L929 cells and kinetics of GIT27-NO. (A) Cells were incubated with different doses of GIT27-NO for 24 h, or alternately (B) with 25 μg/ml of GIT27-NO for kinetic evaluation and LDH release assay was performed (*$p<0.05$). (C). After 24 h incubation with 25 μg/ml of GIT27-NO, the cells were stained with PI and cell cycle was analyzed by flow cytometry. (D). The cells were treated with 25 μg/ml of GIT27-NO for 24 h, and nuclear morphology characteristic of apoptosis (arrows) was examined by fluorescence microscopy after PI staining.
Figure 3:
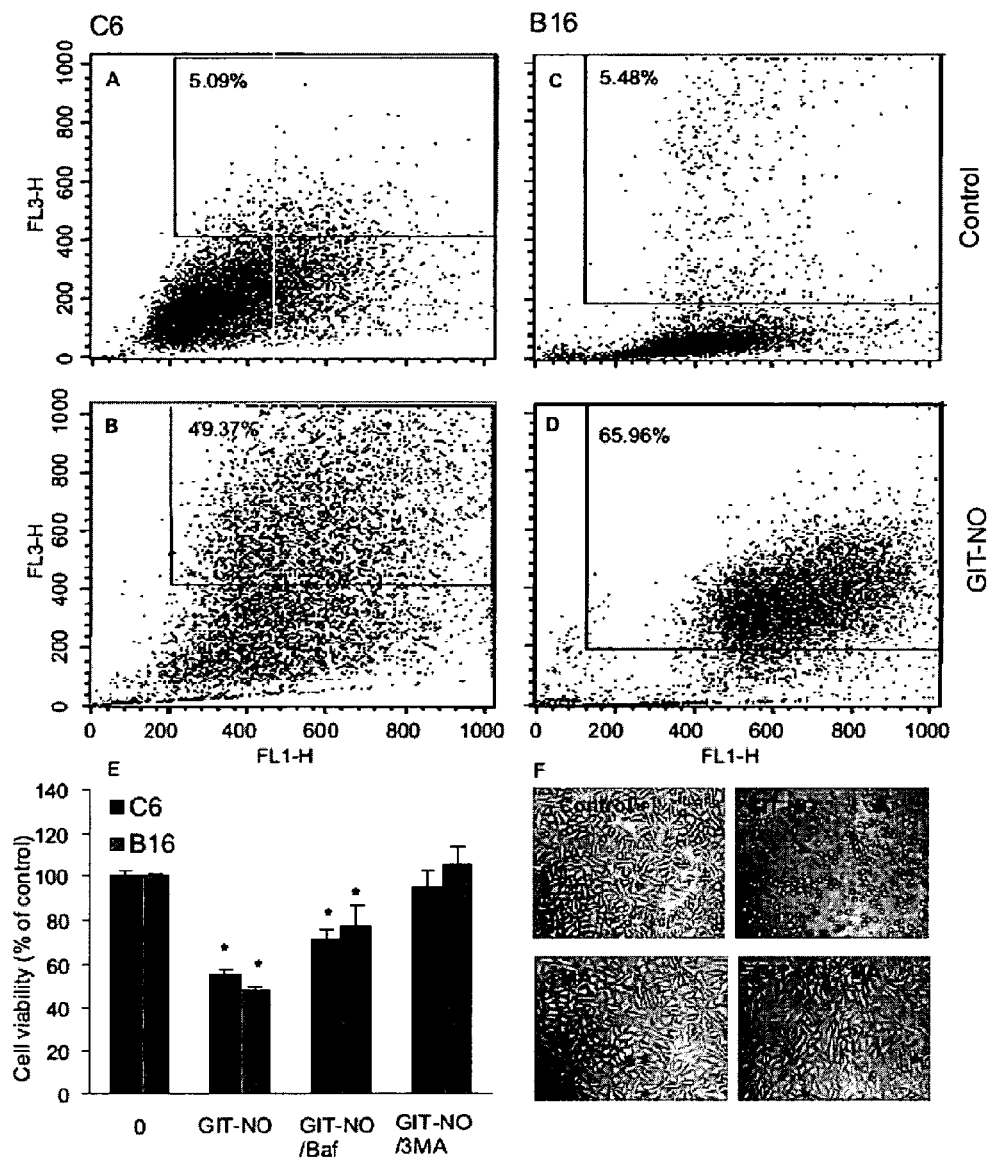
FIG. 3. GIT27-NO induces autophagic cell death in C6 and B16 cells. (A-D) After 24 h cultivation without or with GIT27-NO (25 μg/ml), C6 and B16 cells were stained with acridin orange and analyzed by flow cytometry for the presence of orange-red acidic autophagic vesicles. (E) Cells were incubated without or with GIT27-NO (25 μg/ml), 3-MA (1 mg/ml), and/or or Baf (0.5 μM) for 24 h, as indicated, and MTT assay was performed. *$p<0.05$ refers to an adequate control. (F) Light micrographs of C6 cells incubated for 24 h without (control) or with GIT27-NO (25 μg/ml) and/or 3-MA (1 mg/ml).

In order to determine the antiproliferative effect of compound (I), we performed flow cytometry analysis of CFSE stained cells during 24 h cultivation with or without GIT27-NO. In spite of significant decrease in the number of viable L929 and B16 cells after treatment with GIT27-NO (FIGS. 1B and C), the cells divided almost at the same frequency as untreated control cells (Table 1), indicating that inhibition of proliferation is not responsible for the observed antitumor effect. In parallel, treatment with GIT27-NO affected the proliferation of C6 cells (Table 1), suggesting that the reduction of viable cells is at least partly mediated by the cytostatic effect of the drug on this cell line. We subsequently analyzed the presence of different types of cell death upon treatment of cells with GIT27-NO. Necrosis was determined by LDH release assay, based on the disturbed permeability of dying cells. As shown in (FIGS. 2A and B), GIT27-NO treatment induced LDH release in all three cell lines tested. LDH release was both dose-dependent (FIG. 2A) and time-dependent (FIG. 2B). However, a significant amount of LDH was detectable after 18 h cultivation with the drug, but not at earlier time points, suggesting that that the observed effect could be ascribed to the end stage of apoptosis (secondary necrosis) rather than to primary necrotic cell death. The analysis of cellular DNA content performed after 24 h cultivation with compound (I) revealed a significantly increased proportion of hypodiploid cells (subG compartment of PI stained cells) in L929 cultures (FIG. 2C). On the other hand, the percentage of C6 and B16 cells in subG compartment after incubation in the presence of GIT27-NO was lower (less then 10%) than in L929 cultures, indicating the importance of other type of cell death in drug-mediated cytotoxicity (FIG. 2C). Furthermore, cell cycle arrest in G0/G1 phase was observed in GIT-27NO treated C6 cells (FIG. 2C). Accordingly, cells with condensed chromatins and shrinked nucleus were visible in drug-exposed cultures, confirming the prevalence of apoptotic cell death in L929 cultures in contrast to B16 and C6 cells (FIG. 2D). We therefore analyzed the alternative way of cell death known as autophagic cell death in C6 and B16 cells after treatment with GIT27-NO. To identify the development of acidic autophagosomes typical of autophagy, we performed flow cytometric analysis of acridin orange stained cells. As shown in FIG. 3A-C, in both cell lines GIT27-NO significantly increased the intensity of bright red fluorescence, showing the development of acidic vesicles. To examine the relevance of autophagic cell death in diminished viability of the cells exposed to compound (I), we treated the cells in parallel with known autophagic inhibitors, bafilomycin A (Baf) and 3-methyl adenin (3-MA). 3-MA inhibited autophagic sequestration through inhibition of PI-3 kinase, while Baf, a vacuolar $H^+$-ATPase inhibitor, blocked the fusion of autophagosomes with lysosomes (Kanzawa 2004). As judged by MTT assay, the viability of GIT27-NO treated cells was recovered in the presence of both autophagic inhibitors tested, thus confirming the contribution of autophagic cell death in GIT27-NO cytotoxicity towards C6 and B16 cells (FIG. 3E). Restored viability of C6 cells in the presence of 3-MA was confirmed by light microscopy (FIG. 3F). Taken together, these results suggest that the capability of inducing different types of cell death in different cancer cells is based on the intrinsic specificity of the cell type, rather than on the properties of GIT27-NO.

TABLE 1

Effect of GIT27-NO on tumor cell proliferation rate

| CFSE[a] | | C6 | B16 | L929 |
|---|---|---|---|---|
| Control | R1[b] | 8.37% | 2.00% | 7.26% |
| | R2[c] | 87.05% | 96.58% | 88.57% |
| GIT27-NO | R1 | 42.53% | 6.90% | 13.23% |
| | R2 | 30.75% | 90.65% | 78.07% |

Figure 4:
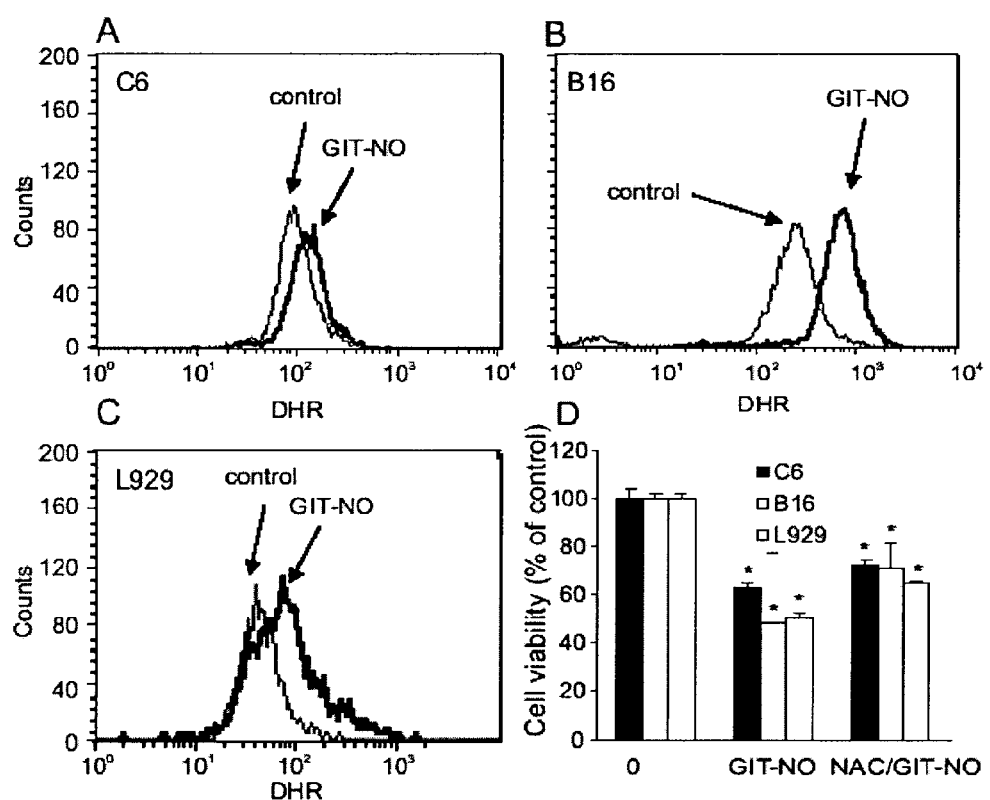
FIG. 4. Involvement of ROS in cytotoxic action of GIT27-NO. (A-C) Cells were incubated in the absence (control) or presence of GIT27-NO (25 μg/ml) and the production of ROS was detected by flow cytometry of DHR fluorescence after 24 h. (D) The viability of cells incubated without or with GIT27-NO (25 μg/ml) in the presence or absence of antioxidant NAC (2.5 μM) was determined after 24 h by MTT assay. *$p<0.05$, refers to an adequate control.

[a] Cells were stained with CFSE immediately before treatment with GIT27-NO (25 μg/ml). After 48 h cell division was estimated by flow cytometry.
[b] R1 = parent population
[c] R2 = divided population Cytotoxicity of GIT27-NO Depends on ROS Generation It is known that oxidative stress triggers cell death. We therefore investigated the role of oxidative stress in the observed cytotoxic action of GIT27-NO. Compared to control cells, intracellular production of ROS was markedly increased after treatment of the cells with GIT27-NO, as estimated by intracellular DHR fluorescence (FIG. 4A-C). Neutralization of ROS by the scavenger NAC restored the viability of GIT27-NO treated cells, indicating that release of ROS was at least partly responsible for the tumoricidal effect of the drug (FIG. 4D).

Figure 5:
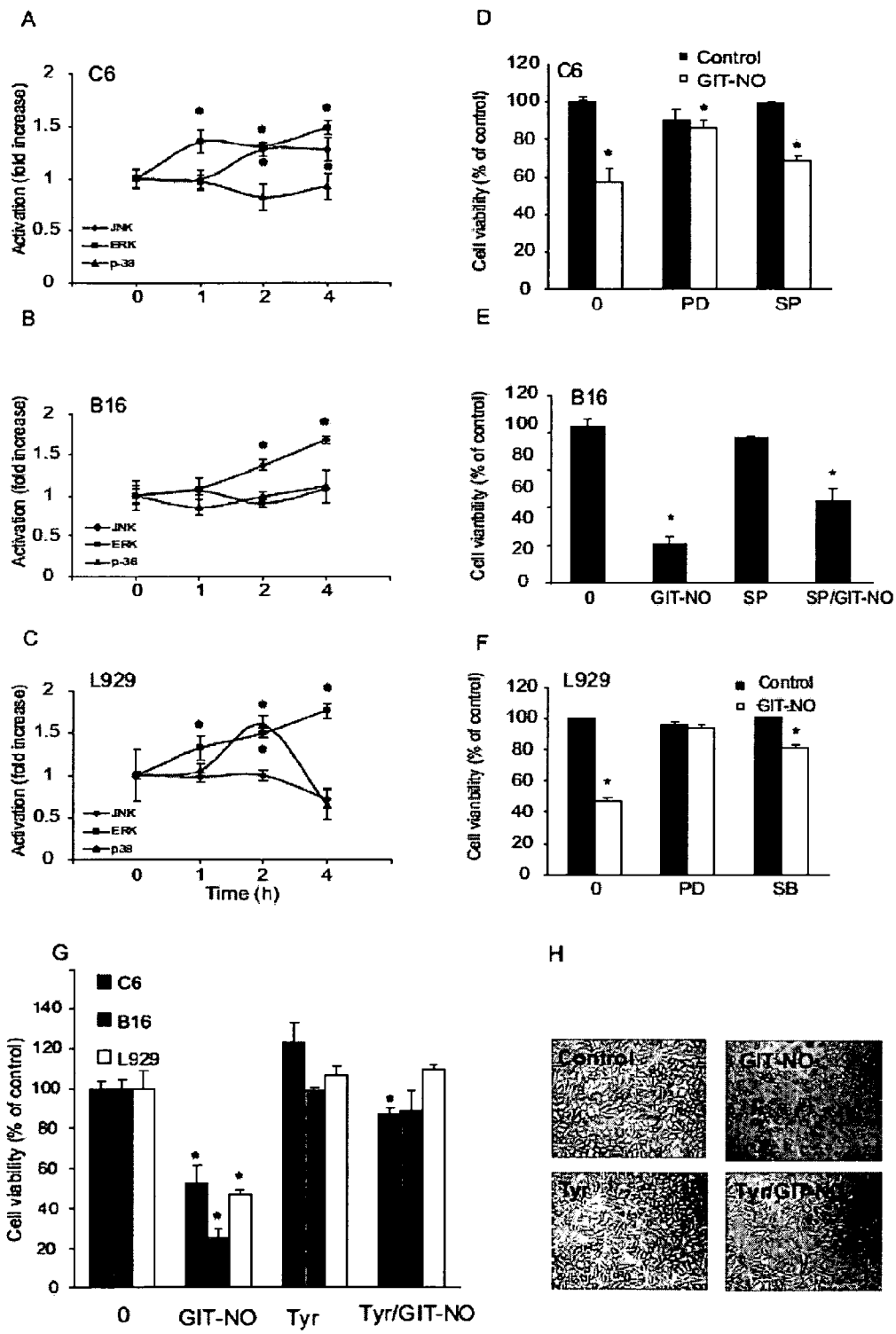
FIG. 5. GIT27-NO differentially regulates MAP kinases and PTK activation. (A-C) Cells were incubated with 25 μg/ml of GIT27-NO and activation of JNK, ERK, and p38 MAPK was assessed by cell-based ELISA at indicated timepoints. The data are presented as fold increase relative to values obtained in untreated control cultures at 0 time point (*p<0.05). (D-G) Cells were incubated without (control) or with GIT27-NO (25 μg/ml) in the presence or absence of specific inhibitors PD98059 (PD, 50 μM), SP600125 (SP, 0.75 μM), SB202190 (SB, 20 μM) or Tyrphostin (Tyr, 5 μM) and MTT assay was performed after 24 h incubation. *p<0.05 refers to an adequate control. (G) Light micrographs of C6 cells incubated for 24 h without (control) or with GIT27-NO (25 μg/ml) and/or of Tyr (5 μM).
Figure 6:
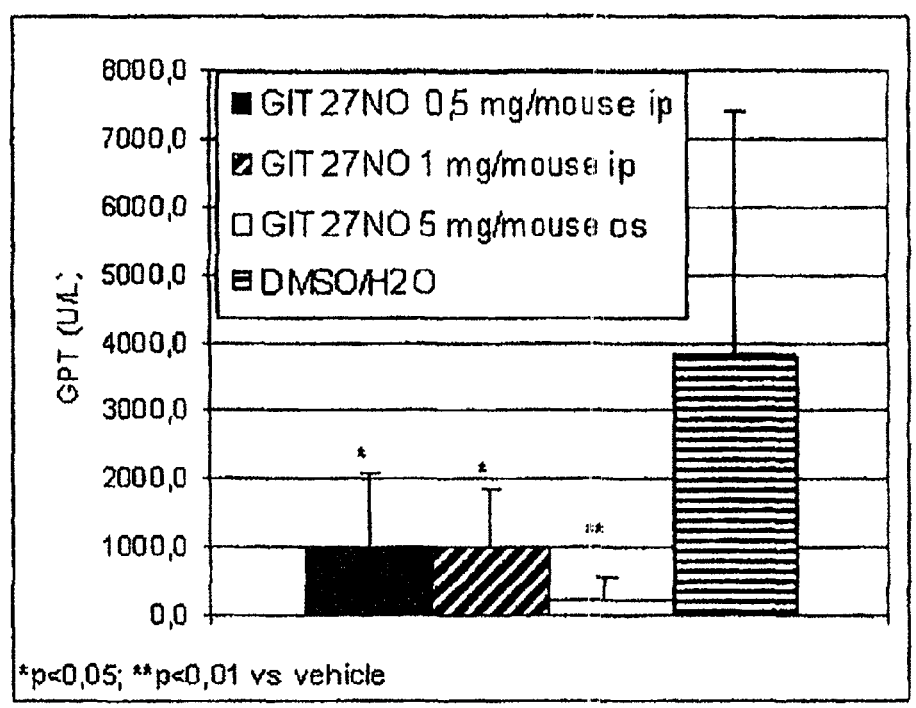
FIG. 6. Shows the reduction of ALT glucose blood levels with prophylactic treatment of GIT27-NO.

GIT27-NO Differentially Regulates Map Kinase Pathways in C6, B16 and L929 Tumor Cells Mitogen-activated protein (MAP) kinases are a family of serine-threonine kinases which is critical for the conversion of extracellular signals to important cellular signals included in survival, proliferation and death (Schindler 2001, Wada 2004, Arbabi 2002). Therefore, we analyzed the influence of GIT27-NO on the activation of these signaling pathways. As determined by cell-based ELISA, different signaling molecules are targets in different cell lines. In C6 cells GIT27-NO induced permanent activation of ERK1/2 and JNK (FIG. 5A). On the other hand, a different pattern was observed in cultures of B16 cells. While GIT27-NO did not affect the activation of ERK1/2 in B16 cells, a significant time-dependent activation of JNK and only slight activation of p38 was observed (FIG. 5B). Finally, treatment of L929 with GIT27-NO led to marked and sustained activation of ERK1/2 and significant transient activation of p38, without affecting the expression of JNK (FIG. 5C). In an effort to assess the biological significance of the activation of MAP kinase in the reduction of cell viability we used known pharmacological inhibitors of these molecules: PD98059 for ERK, SP600125 for JNK, and SB202190 for p38 activation. Before incubation with GIT27-NO, the cells were pulsed for 30 min with each of these inhibitors and viability was estimated by MTT after 24 h of cultivation. Treatment of C6 cells with specific ERK and JNK inhibitors (FIG. 5D), B16 cells with JNK inhibitor (FIG. 5E), and L929 cells with ERK and p38 inhibitors (FIG. 5F) significantly improved the survival of tumor cell lines, confirming the role of these molecules in drug-mediated cytotoxicity. The data thus suggest that the ability of GIT27-NO to trigger different molecules in the signaling cascade is mainly determined by the cell type. To examine the influence of upstream signaling molecules we treated the cells with protein tyrosin kinase (PTK) inhibitor, tyrphostin, in parallel with GIT27-NO. As shown in FIG. 5G, inhibition of PTK almost completely restored the viability of all tested cell lines, indicating the same target position of drug action. The effect of tyrphostin on GIT27-NO treated C6 cells was visualized by light microscopy (FIG. 5H).

GIT27-NO Inhibits the Tumor Growth in C57BL/6 Mice Bearing B16 Melanoma

Having demonstrated the cytotoxic properties of GIT27-NO in vitro, we evaluated its in vivo anti-tumor properties in B16 melanoma-bearing mice. As illustrated in Table 2, a short-course treatment with GIT27-NO (0.5 mg/mouse/day for 10 days), started on day 10 after tumor implantation when the first tumor was palpable, was associated with a significant reduction of tumor growth as compared to untreated control animals. The effect was stable even after interruption of administration of GIT27-NO. Only 2 animals died in the control group, while all animals treated with GIT27-NO survived 30 days of follow-up period (not shown). Taken together, the cytotoxic properties of GIT27-NO toward B16 melanoma cells are associated with its in vivo anti-tumor effects.

TABLE 2

Effects of in vivo GIT27-NO treatment on B16 melanoma tumor growth

| Group | Number of animals | Mean tumor volume[a] |
|---|---|---|
| Control | 27 | 2.97 ± 6.4 |
| GIT27-NO | 25 | 0.82 ± 1.2* |

[a] Tumor volumes were determined at the end of follow-up period (30 days after B16 melanoma cell implantation) and calculated as indicated in Materials and methods.
*p < 0.05, refers to control animals treated with vehicle only.

GIT27-NO Reduces ALT Glucose Blood Levels in ConA-Induced Hepatitis

At all the tested dose the prophylactic treatment with Git27-NO significantly reduced ALT glucose blood levels when compared to vehicle treated mice.

DISCUSSION

This study shows that chemical modification of VGX-1027 allows to obtain a novel NO-donating compound with strong tumoricidal potential. Treatment of tree different cell lines, L929 mouse fibrosarcoma, C6 rat astrocytoma and B16 melanoma with modified substance GIT27-NO led to dramatical reduction of their viability. In contrast, the parent compound VGX-1027 did not affect tumor cell growth in the same or higher (data not shown) concentration range as GIT27-NO. The anti-tumor effects of GIT27-NO are not mediated by its cytostatic effects but are rather based on its ability of triggering the cascade of intracellular events resulting in cell death induction. However, the C6 cell line represented an exception, since GIT27-NO caused arrest of cell division in the G0/G1 phase. Numerous evidences revealed strong antineoplastic properties of modified antiinflammatory nonsteroidal drugs by covalent attachment of NO (Rigas 2004). For example, significant growth reduction of human bladder, prostate, colon cancer and Jurkat leukemia cells were observed upon treatment with different NO-NSAIDs (Kashfi et al 2003, Yeh 2004, Huguenin 2005, Huguenin 2004, Huguenin 2004, Gao 2005, Nath 2004, Spiegel 2005). We observed that decreased viability of the cells was followed by release of LDH which is regarded as a typical feature of necrotic cell death. However, necrosis was observed after 18 h incubation in the presence of the drug suggesting that LDH release could be mainly attributed to secondary apoptosis rather then to primary necrosis. The most frequent mechanism in anticancer drugs action is induction of apoptosis (Ferreira 2002). There is plenty of evidence of tumor cell resistance to apoptotic cell death (Kim 2005). This phenomenon could be explained by the over-expression of signaling molecules with antiapoptotic properties (Gabriel 2003). An extremely interesting feature of GIT27-NO is its potential to adapt the tumoricidal mechanism to cell specificity. The L929 cell line, which is of mesodermal origin, mainly died through apoptosis. Accordingly, it was reported that NO-aspirin is capable of inducing apoptosis in colon cancer cells, while the other drug, NO-sulindac is responsible for apoptotic death of bladder and prostate carcinoma (Gao 2005, Huguening 2004). In contrast to L929 cells, only a small amount of hypodiploid cells was detected in C6 and B16 cells treated with GIT27-NO. On the other hand, GIT27-NO induced autophagy in cultures of C6 and B16 cell lines. Induction of autophagy as a mode of action of radiation and anticancer drugs, such as tamoxifen, aloe-emodin, arsenic trioxide and others was recently reported (Mijatovic 2005, Kanzawa 2004, 2003, Bilir, Paglin, Gorka). Treatment of cells with specific inhibitors, 3-MA and bafilomycin A restores cell viability, confirming that under our condition autophagy serves as a destroying rather than as a salvaging mechanism. Efficient rescue of the cells against GIT27-NO induced toxicity by known PI-3K inhibitor, 3-MA, pointed out the importance of this pathway, which could be the subject of further research. Interactions between apoptotic and autophagic cell death are well documented. These two types of cell death could coexist in the cell and, depending on the circumstances, they could trigger or inhibit each other (Kim 2006). However, although aloe-emodin is considered as an apoptotic inducing agent, we have found that this drug preferentially acts through induction of autophagic cell death in glioma cell lines (Pecere 2000, CMLS 2005). It is interesting that GIT27-NO is not capable of spontaneously releasing NO, as exogenous donors do, but in the presence of cells significant amount of nitrite could be detected. Thus, it is obvious that for NO release GIT27-NO requires contact with cells. Moreover, NO-scavenger hemoglobin almost completely neutralized the effect of this compound, confirming the crucial role of NO in the suppression of tumor growth. It is known that NO is a highly reactive species with strong affinity for thiol groups of free aminoacids, peptides or proteins, electron-donating properties and/or ability to form new free radicals (Schindler 2001). It was previously shown that ROS and RNS mediate apoptotic and autophagic cell death (Li 2005, Kanzawa 2004, Erdal 2005). Treatment of cells with VGX-1027 did not release ROS (data not shown) while significant amounts of ROS were determined in the presence of GIT27-NO. DHR also detected peroxinitrite, which is the product of reaction of $O_2^-$ and NO and is actually one of the most reactive and destroying molecule (Lechner 2005, Li 2005). It is evident that NO release triggered the production of reactive radicals and, as a consequence, led to reduction of cell viability, which was further verified by treatment with the antioxidant NAC. In line with our study, Gao et al. showed that NO-donating aspirin induced apoptosis in human colon cancer cells through induction of oxidative stress. (Gao PNAS). Moreover, it is known that NO dramatically modulates the activity of enzymes and transcription factors and consequently alters cell signaling pathways involved in the regulation of proliferation, differentiation and cell death processes (Schindler 2001). The anti-tumor effect of NO-donating aspirin is mediated by activation of MAP kinases (Hundley 2005). These authors reported that the NO-donating drug activated JNK and p38 in colon cancer cells and therefore led to activation of AP-1 complex, whereas inhibition of these kinases by specific inhibitors partially blocked the cytotoxic effect of the drug. GIT27-NO differentially modified the activity of members of the MAP kinase family depending on the cell type. While in L929 cells GIT27-NO induced strong time dependent up-regulation of ERK1/2, followed by transient up-regulation of p-38, treatment of B16 cells with the same agent resulted in strong phosphorilation of JNK and only in slight increase of p38. C6 glioma cells simultaneously up-regulated JNK and ERK during the treatment, while the activity of p38 was not affected. It is hypothesized that the variation of the cell response to GIT27-NO is related to the cell-death mechanism. It is known that strong activation of ERK1/2 in L929 cells induced by cisplatin leads cells to apoptosis, and its suppression neutralized the anti-tumor potential of the drug. Therefore, up-regulated ERK1/2 could be the possible reason for preferential apoptosis of L929 cells upon treatment with GIT27-NO. It is worth mentioning that PTK inhibition in all three tested cell lines counteracted the cytotoxicity of the drug. This evidenced that the drug action was the same at the outset and that differences could result from the activation of different signaling pathways in each cell line. We have already mentioned that NO-NSAIDs are highly promising class of drugs for several disorders, including cancer (Rigas 2004 rew). NO-NSAIDs prevented intestinal carcinogenesis in Min mice, rat model of colon cancer and also pancreatic cancer in a hamster tumor model (Ouang, Bak, Williams, Rao). It should be remarked that GIT27-NO significantly suppressed the growth of B16 melanoma in C57BL/6 mice. Functional transformation of the parent compound determined strong tumoricidal properties mainly mediated by NO. The adaptability of the mechanism of action to each type of treated cells is advantageous in comparison with other chemotherapeutic. Our results could be a starting point for further investigation of possible therapeutic uses of compound (I).

REFERENCES

Del Soldato P, Sorrentino R, Pinto A. NO aspirins: a class of new antiinflammatory and antithrombotic agents. Thrends Pharmacol Sci 1999; 20(8): 319-23.

Mijatovic S, Maksimovic-Ivanic D, Radovic J, Miljkovic Dj, Harhaji Lj, Vuckovic O, Stosic-Grujicic S, Mostarica Stojkovic M, Trajkovic V. Anti-glioma action of aloe emodin: the role of ERK inhibition. Cell. Mol. Life. Sci 2005; 62: 589-98.

Mijatovic S, Maksimovic-Ivanic D, Radovic J, Popadic D, Momcilovic M, Harhaji Lj, Miljkovic D, Trajkovic V. Aloe-emodin prevents cytokine-induced tumor cell death: the inhibition of auto-toxic nitric oxide release as a potential mechanism. Cell Mol. Life. Sci. 2004; 61:1805-15.

Kang W, Nielsen O, Fenger C, Leslie G, Holmskov U, Reid κB. Induction of DMBT1 expression by reduced ERK activity during a gastric mucosa differentiation-like process and its association with human gastric cancer. Carcinogenesis 2005; 26:1129-37.

Decker T, Lohmann-Matthes M L. A quick and simple method for the quantitation of lactate dehydrogenase release in measurements of cellular cytotoxicity and tumor necrosis factor (TNF) activity. J Immunol Methods 1998; 115: 61-9.

Kaludjerovic G N, Miljkovic D, Momcilovic M, Djinovic V M, Mostarica Stojkovic M, Sabo T J, Trajkovic V. Novel platinum(IV) complexes induce rapid tumor cell death in vitro. Int J Cancer 2005; 116:479-86.

Smagur A, Szary J, Szala S. Recombinant angioarrestin secreted from mouse melanoma cells inhibits growth of primary tumours. Acta Biochim Pol 2005; 52:875-9.

Kanzawa T, Germano I M, Komata T, Ito H, Kondo Y, Kondo S. Role of autophagy in temozolomide-induced cytotoxicity for malignant glioma cells. Cell Death Differ 2004; 11:448-57.

Versteeg H. H., Nijhuis E., van den Brink G. R., Evertzen M., Pynaert G. N., et al. (2000) A new phosphospecific cell-based ELISA for p42/p44 mitogen-activated protein kinase (MAPK), p38 MAPK, protein kinase B and cAMP-response-element-binding protein. Biochem. J. 350: 717-22.

Rao C V, Reddy B S, Steele V E, Wang C X, Liu X, Ouyang N, Patlolla J M, Simi B, Kopelovich L, Rigas B. Nitric oxide-releasing aspirin and indomethacin are potent inhibitors against colon cancer in azoxymethane-treated rats: effects on molecular targets. Mol Cancer Ther. 2006 June; 5(6):1530-8.

Ouyang N, Williams J L, Tsioulias G J, Gao J, Iatropoulos M J, Kopelovich L, Kashfi K, Rigas B. Nitric oxide-donating aspirin prevents pancreatic cancer in a hamster tumor model. Cancer Res. 2006 Apr. 15; 66(8):4503-11.

Gao J, Liu X, Rigas B. Nitric oxide-donating aspirin induces apoptosis in human colon cancer cells through induction of oxidative stress. Proc Natl Acad Sci USA. 2005 Nov. 22; 102(47):17207-12.

Hundley T R, Rigas B. Nitric oxide-donating aspirin inhibits colon cancer cell growth via mitogen-activated protein kinase activation. J Pharmacol Exp Ther. 2006 January; 316(1):25-34.

Spiegel A, Hundley T R, Chen J, Gao J, Ouyang N, Liu X, Go M F, Tsioulias G J, Kashfi K, Rigas B. NO-donating aspirin inhibits both the expression and catalytic activity of inducible nitric oxide synthase in HT-29 human colon cancer cells. Biochem Pharmacol. 2005 Oct. 1; 70(7):993-1000.

Nath N, Labaze G, Rigas B, Kashfi K. NO-donating aspirin inhibits the growth of leukemic Jurkat cells and modulates beta-catenin expression. Biochem Biophys Res Commun. 2005 Jan. 7; 326(1):93-9.

Rigas B, Kashfi K. Nitric-oxide-donating NSAIDs as agents for cancer prevention. Trends Mol. Med. 2004 July; 10(7): 324-30.

Yeh R K, Chen J, Williams J L, Baluch M, Hundley T R, Rosenbaum R E, Kalala S, Traganos F, Benardini F, del Soldato P, Kashfi K, Rigas B. NO-donating nonsteroidal antiinflammatory drugs (NSAIDs) inhibit colon cancer cell growth more potently than traditional NSAIDs: a general pharmacological property? Biochem Pharmacol. 2004 Jun. 15; 67(12):2197-205.

Williams J L, Kashfi K, Ouyang N, del Soldato P, Kopelovich L, Rigas B. NO-donating aspirin inhibits intestinal carcinogenesis in Min (APC(Min/+)) mice. Biochem Biophys Res Commun. 2004 Jan. 16; 313(3):784-8.

Kashfi K, Ryan Y, Qiao L L, Williams J L, Chen J, Del Soldato P, Traganos F, Rigas B. Nitric oxide-donating nonsteroidal anti-inflammatory drugs inhibit the growth of various cultured human cancer cells: evidence of a tissue type-independent effect. J Pharmacol Exp Ther. 2002 December; 303(3):1273-82.

Stosic-Grujicic S, Cvetkovic I, Mangano K, Fresta M, Maksimovic-Ivanic D, Harhaji L, Popadic D, Momcilovic M, Miljkovic D, Kim J, Abed Y A, Nicoletti F. A Potent Immunomodulatory Compound, (S,R)-3-Phenyl-4,5-dihydro-5-isoxasole Acetic Acid, Prevents Spontaneous and Accelerated Forms of Autoimmune Diabetes in NOD Mice and Inhibits the Immunoinflammatory Diabetes Induced by Multiple Low Doses of Streptozotocin in CBA/H Mice. J Pharmacol Exp Ther. 2007 March; 320(3):1038-49.

Huguenin S, Vacherot F, Fleury-Feith J, Riffaud J P, Chopin D K, Bolla M, Jaurand M C. Evaluation of the antitumoral potential of different nitric oxide-donating non-steroidal anti-inflammatory drugs (NO-NSAIDs) on human urological tumor cell lines. Cancer Lett. 2005 Feb. 10; 218(2): 163-70.

Huguenin S, Fleury-Feith J, Kheuang L, Jaurand M C, Bolla M, Riffaud J P, Chopin D K, Vacherot F. Nitrosulindac (NCX 1102): a new nitric oxide-donating non-steroidal anti-inflammatory drug (NO—NSAID), inhibits proliferation and induces apoptosis in human prostatic epithelial cell lines. Prostate. 2004 Oct. 1; 61(2):132-41.

Huguenin S, Vacherot F, Kheuang L, Fleury-Feith J, Jaurand M C, Bolla M, Riffaud J P, Chopin D K. Antiproliferative effect of nitrosulindac (NCX 1102), a new nitric oxide-donating non-steroidal anti-inflammatory drug, on human bladder carcinoma cell lines. Mol Cancer Ther. 2004 March; 3(3):291-8.

Bak A W, McKnight W, Li P, Del Soldato P, Calignano A, Cirino G, Wallace J L. Cyclooxygenase-independent chemoprevention with an aspirin derivative in a rat model of colonic adenocarcinoma. Life Sci. 1998; 62(23):PL 367-73.

Schindler H, Bogdan C. NO as a signaling molecule: effects on kinases.

Int Immunopharmacol. 2001 August; 1(8):1443-55.

Kanzawa T, Kondo Y, Ito H, Kondo S, Germano I. Induction of autophagic cell death in malignant glioma cells by arsenic trioxide. Cancer Res 2003; 63: 2103-8.

Bilir A, Altinoz M A, Erkan M, Ozmen V, Aydiner A. Autophagy and nuclear changes in FM3A breast tumor cells after epirubicin, medroxyprogesterone and tamoxifen treatment in vitro. Pathobiology 2001; 69:120-6.

Paglin S, Hollister T, Delohery T, Hackett N, McMahill M, Sphicas E, Domingo D, Yahalom J. A novel response of cancer cells to radiation involves autophagy and formation of acidic vesicles. Cancer Res 2001; 61: 439-44.

Gorka M, Daniewski W M, Gajkowska B, Lusakowska E, Godlewski M M, Motyl T. Autophagy is the dominant type of programmed cell death in breast cancer MCF-7 cells exposed to AGS 115 and EFDAC, new sesquiterpene analogs of paclitaxel. Anticancer Drugs 2005; 16:777-88.

Kim R, Emi M, Tanabe K, Murakami S, Uchida Y, Arihiro Regulation and interplay of apoptotic and non-apoptotic cell death J. Pathol. 2006 February; 208(3):319-26.

Pecere T, Gazzola M V, Mucignat C, Parolin C, Vecchia F D, Cavaggioni A, Basso G, Diaspro A, Salvato B, Carli M, Palu G. Aloe-emodin is a new type of anticancer agent with selective activity against neuroectodermal tumors. Cancer Res 2000; 60: 2800-4.

Mijatovic S, Maksimovic-Ivanic D, Radovic J, Miljkovic D, Kaludjerovic G N, Sabo T J, Trajkovic V. Aloe emodin decreases the ERK-dependent anticancer activity of cisplatin. Cell Mol. Life. Sci. 2005 June; 62(11):1275-82.

Tarr J M, Eggleton P, Winyard P G. Nitric oxide and the regulation of apoptosis in tumour cells. Curr Pharm Des. 2006; 12(34):4445-68.

Hofseth L J, Hussain S P, Wogan G N, Harris C C. Nitric oxide in cancer and chemoprevention. Free Radic Biol Med. 2003 Apr. 15; 34(8):955-68.

Keeble J E, Moore P K. Pharmacology and potential therapeutic applications of nitric oxide-releasing non-steroidal anti-inflammatory and related nitric oxide-donating drugs. Br J. Pharmacal. 2002 October; 137(3):295-310.

Wada T, Penninger J M. Mitogen-activated protein kinases in apoptosis regulation. Oncogene. 2004 Apr. 12; 23(16):2838-49.

Erdal H, Berndtsson M, Castro J, Brunk U, Shoshan M C, Linder S. Induction of lysosomal membrane permeabilization by compounds that activate p53-independent apoptosis. Proc Natl Acad Sci USA. 2005 Jan. 4; 102(1):192-7.

Mitra R, Singh S, Khar A: Antitumour immune responses. Expert Rev Mol. Med. 2003 Jan. 13; 2003:1-22.

Gabriel B, Sureau F, Casselyn M, Teissie J, Petit P X. Retroactive pathway involving mitochondria in electroloaded cytochrome c-induced apoptosis. Protective properties of Bcl-2 and Bcl-XL. Exp Cell Res. 2003 Oct. 1; 289(2):195-210.

Li C Q, Wogan G N. Nitric oxide as a modulator of apoptosis. Cancer Lett. 2005 Aug. 8; 226(1):1-15.

Lechner M, Lirk P, Rieder J. Inducible nitric oxide synthase (iNOS) in tumor biology: the two sides of the same coin. Semin Cancer Biol. 2005 August; 15(4):277-89.

Ferreira C G, Epping M, Kruyt F A, Giaccone G. Apoptosis: target of cancer therapy.

Clin Cancer Res. 2002 July; 8(7):2024-34.

Ivana Stojanovic; Salvatore Cuzzocrea; Katia Mangano; Emanuela Mazzon; Djordje Miljkovic; Mingjun Wang; Marco Donia; Yousef Al Abed; Joseph Kim; Stanislava Stosic-Grujicic; Mogens Claesson. In vitro, ex vivo and in vivo immunopharmacological activities of the isoxazoline compound VGX-1027: Modulation of cytokine synthesis and prevention of both organ-specific and systemic autoimmune diseases in murine models. Clin Immunol, in press.

The invention claimed is:

1. A compound of formula (I)

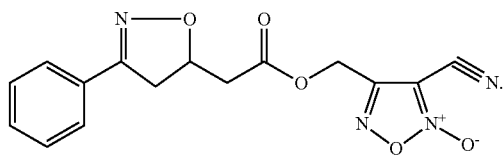

(I)

2. A compound of formula (II)

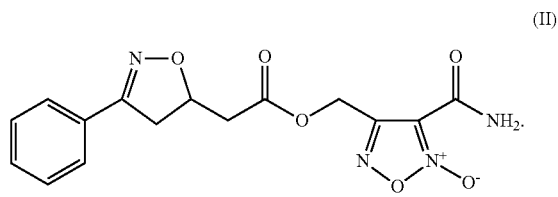

(II)

3. Pharmaceutical compositions containing the compound of claim 1 in admixture with suitable excipients and/or vehicles.

4. Pharmaceutical compositions containing the compound of claim 2 in admixture with suitable excipients and/or vehicles.

5. A method for the treatment of cancer selected from the group consisting of soft tissue cancer, skin cancer, and brain cancer, comprising administering a therapeutically effective amount of the compound of claim 1.

6. A method for the treatment of hepatitis comprising administering a therapeutically effective amount of the compound of claim 1.

7. A method for the treatment of cancer selected from the group consisting of soft tissue cancer, skin cancer, and brain cancer, comprising administering a therapeutically effective amount of the compound of claim 2.

8. A method for the treatment of hepatitis comprising administering a therapeutically effective amount of the compound of claim 2.

* * * * *